United States Patent

Cruanas et al.

[11] Patent Number: 6,022,317
[45] Date of Patent: Feb. 8, 2000

[54] EQUIPMENT FOR THE TREATMENT OF CAPSULAR CONTRACTURES IN MAMMAL BREAST IMPLANTS AND ITS PROCESS OF APPLICATION

[75] Inventors: Jose Colls Cruanas; Jorge Planas Ribo, both of Terrassa, Spain

[73] Assignee: Medicina en Forma, S.L., Spain

[21] Appl. No.: 09/099,500

[22] Filed: Jun. 18, 1998

[30] Foreign Application Priority Data

Jun. 20, 1997 [ES] Spain .................................. 9701347

[51] Int. Cl.⁷ ...................................................... A61B 8/00
[52] U.S. Cl. .............................. 600/439; 601/2; 606/31
[58] Field of Search ........................ 623/7, 8; 450/38–40, 450/54, 55; 600/439, 438; 606/31, 33, 34, 41; 607/99; 514/57; 601/2, 3

[56] References Cited

U.S. PATENT DOCUMENTS

| | | | |
|---|---|---|---|
| 4,513,750 | 4/1985 | Heyman et al. | 600/438 |
| 4,636,213 | 1/1987 | Pakiam | 623/8 |
| 4,805,628 | 2/1989 | Fry et al. | 600/458 |
| 5,068,225 | 11/1991 | Pennell et al. | 514/57 |
| 5,458,596 | 10/1995 | Lax et al. | 606/31 |
| 5,785,705 | 7/1998 | Baker | 606/32 |

*Primary Examiner*—William E. Kamm
*Assistant Examiner*—Ali M. Imam
*Attorney, Agent, or Firm*—Ostrolenk, Faber, Gerb & Soffen, LLP

[57] ABSTRACT

The invention refers to an equipment (10) for the generation of ultrasonic waves with regulation of the frequency and power range with two possibilites of working, i.e. in continuous or pulsating modes, to be transmitted by adequate means to the transducers (14), The invention discloses a supporting means such as a harness (16) or similar. Said harness (16) is directly applied on the breast with capacity to act on the same in a selective way by programming the amount of power to be transmitted to transducers (14) in an individualized form. The invention permits the elimination of capsular contractures corresponding to degree IV in the Baker scale.

12 Claims, 2 Drawing Sheets

EQUIPMENT FOR THE TREATMENT OF CAPSULAR CONTRACTURES IN MAMMAL BREAST IMPLANTS AND ITS PROCESS OF APPLICATION

This invention refers, according to its title, to an "EQUIPMENT FOR THE TREATMENT OF CAPSULAR CONTRACTURES IN MAMMAL IMPLANTS AND ITS PROCESS OF APPLICATION", which novelty characteristics by its design and construction specifically fulfil the object of the invention, bringing out remarkable safety and efficiency to its function.

The rejection problems arising after surgical feminine breasts have as principal outcome the formation of different degrees of plate-like calcifications surrounding the prosthesis which have been implanted, this leading in some cases to new surgical interventions in case the so called "capsulation" or capsular contracture appears.

Said rejection processes appear either after one week from the intervention or after approximately one year, no explanation having been found so far for this spread in time of the appearance of rejection symptoms so that the reasons for the same are currently unknown. Although the progress in the design of the implants and the selection of adequate materials for the prosthesis has contributed to a reduction of the capsular contracture cases, its percentage is still important and the Health authorities in many countries have recommended prevention measures to try to cope with these rejection problems.

Currently, when the capsulation problem starts to be clinically appreciable it is usual to proceed to an standard treatment by means of massages of various degrees of intensity applied to the breast. Some investigations, as those carried out by Dr. Baker, which gave ground to a clinical treatment known by his name, have evidenced that although said massaging treatment may constitute a temporary solution for some cases, it does not prevent the relapse of the disturbance.

The present invention addresses the rejection problems and the formation of the above mentioned capsules avoiding the current manual treatments as well as the surgical interventions needed in some cases. The invention provides a treatment by ultrasonic waves which is totally eternal to the body and which has revealed a high effectivity to counter the biological mechanisms giving ground to the formation of said capsules, which treatment, carried out with other embodiments, parameters and equipments, has brought already meaningful results in problems like cellulitis, keloid scars and other similar disturbances.

An additional object of the present invention is a process for the application of the equipment, with the aim to overcome the different degrees of capsular contractures by means of the corresponding routines.

Two years ago the inventors started tests for the application of an eternal treatment by means of ultrasonic waves with the apparatus which is the subject of the present invention, which have yielded the results which have been summarized in the following. The invention has been found to be effective for the most severe cases of capsule formation on the implants and in the prevention of relapse.

The tests with the apparatus which is the subject of the present invention have been carried out with a panel of 24 patients with ages comprised between 24 and 52 years with a total of 34 implants in the breasts (14 unilateral and 10 bilateral), classified in various degrees of "contracture" according to the Baker scale shown in table

TABLE I

Distribution of the contractures before the treatment according to the Baker scale

| | | |
|---|---|---|
| IV | 11 | 32.4 |
| III | 22 | 64.6 |
| II | 1 | 3 |
| Total | 34 | 100 |

Eighteen of the patients had been submitted to subglandular implants, three to retropectoral implants, two of the patients had been submitted to post-mastectomy reconstructions by means of implants and finally, in one case the patient had an unknown type of prosthesis.

Of the thirty-four prosthesis implanted, 23 of them were silica gel implants, 4 were soybean oil implants and other 7 were implants of unknown origin. The capsulations had been developed within periods of time comprised between 22 weeks and 4 years with an average of six months approximately after the surgical intervention for the implantation of said prosthesis.

All of the breasts with contractures had suffered a first capsule formation according to the technical compression method proposed by Baker in 1976. In three of the cases with contractures corresponding to class IV, the manual treatment was not satisfactory. However, after a mild session with ultrasonic waves generated by the apparatus of the invention the breaking of the contractures was effective.

The ultrasonic waves generating apparatus was connected to eight transducers for the emission of ultrasound with a variable output power regulatable between 1 to 15 watts, generating a maximum power with a density of 3 watts/cm$^2$ with a working frequency of 0.15 to 7 MHz.

Four transducers were applied on each breast, oriented towards the capsule and attached to a special harness, see FIG. 2.

The ultrasonic waves generator of the invention will have two working modalities, that is, a continuous and a pulsating mode. In any case, after determination of the value of the emitted power per each outlet, the same apparatus will automatically determine the duration of the cycle and the distributions needed by the transducers. Where the regulatable pulsating system is used for the treatment in subglandular or retropectoral situation, the emission cycle is five times longer in order to minimise the effects of ultrasonic waves energy on biologic tissues. To supply the same energy amount, the pulsating system has been initially used. Subsequently this system has been preferred for future investigations because of the better clinical results which have been obtained in the softening of the capsules and preventing any disagreeable effects to the patients for an excess of heating.

One of the preferred solutions used in the ultrasonic waves generator according to the invention consists in using a power outlet of 15 watts for each cycle with a power density in anyone of the transducers of 600 mW/cm$^2$. The number of cycles for the ultrasonic waves application has been modified taking into account the importance of the contracture and the number of sessions of treatment by ultrasonic waves, considering the clinical response. The treatment by means of ultrasonic waves has been programmed twice a week being extended until stable and satisfactory results have been obtained. The treatment sessions needed for an average of 5.27 are determined with the application of ultrasounds from 15 to 36 cycles per session.

TABLE II

Distribution pre and post-treatment of the contractures according to the Baker scale showing the improvement percentages for each degree

| Baker scale initial degree | Cases | Baker scale final degree and improvement percentages | | | |
|---|---|---|---|---|---|
| | | I | II | III | IV |
| II | 1 | 1 (100%) | 0 | | |
| III | 22 | 19 (86.36%) | 2 (9.09%) | 1 (4.54%) | |
| IV | 11 | 8 (72.72%) | 1 (9.09%) | 2 (18.18%) | 0 |

TABLE III

Improvement percentage after one year of continuous treatment

| Baker scale degree | Contractures | % |
|---|---|---|
| IV | 0 | 0 |
| III | 2 | 5.91 |
| II | 2 | 11.82 |
| I | 28 | 82.27 |

The results obtained with the application of the inventive technique with repeated application of ultrasonic waves energy and the results of the follow-up monitoring during 12 months of treatment are reflected in tables II and III. During the tests no complications were experienced. The patients felt after the treatment with ultrasonic waves a subjective softening of the breast with no disagreeable sensation from an excess of heat. In three of the cases corresponding to class IV in the Baker scale, the compression of the capsulation was eliminated after only one (ultrasonic waves) treatment session. The most extensive long term report on the results of capsulotomy by closed compression was published by Little and Baker in 1980. These investigators made a report on a broad sample of patients in which the highest relapse rate in post-treatment capsular contracture was to be found around six months after treatment and the total relapse rate after 12 months was established with a percentage of at least 33%. Only 67% of the patients submitted to treatment, regardless of the seriousness of the pre-treatment contractures, obtained satisfactory and long lasting results.

In the test carried out by the present inventors although with a lower number of patients, 8227% of the patients were free from clinical signs of capsular contracture after 12 months of follow-up monitoring (see Table III). Further, these data have to be considered taking into account the seriousness of the contractures under treatment. According to the Baker report, the rate of serious cases may be evaluated (degrees III and IV) approximately at 62%, which percentage is really low in comparison to the series of tests carried out by the inventors (97%, see Table I).

Other details and characteristics of the present invention will be evidenced by means of the following description which refers to the attached drawings in which the relevant details are diagrammatically shown. These details are only illustrative examples referred to a possible embodiment of the invention which will not limited to the details of this description. Therefore, the present description has to be taken into account as an illustrative example without any undue limitations.

The following reference numerals correspond to the description and attached drawings: (10) piece of equipment, (11) display, (12) control system, (13) power source, (14) transducer, (15) keyboard, (36) attachment harness.

Figure 1:
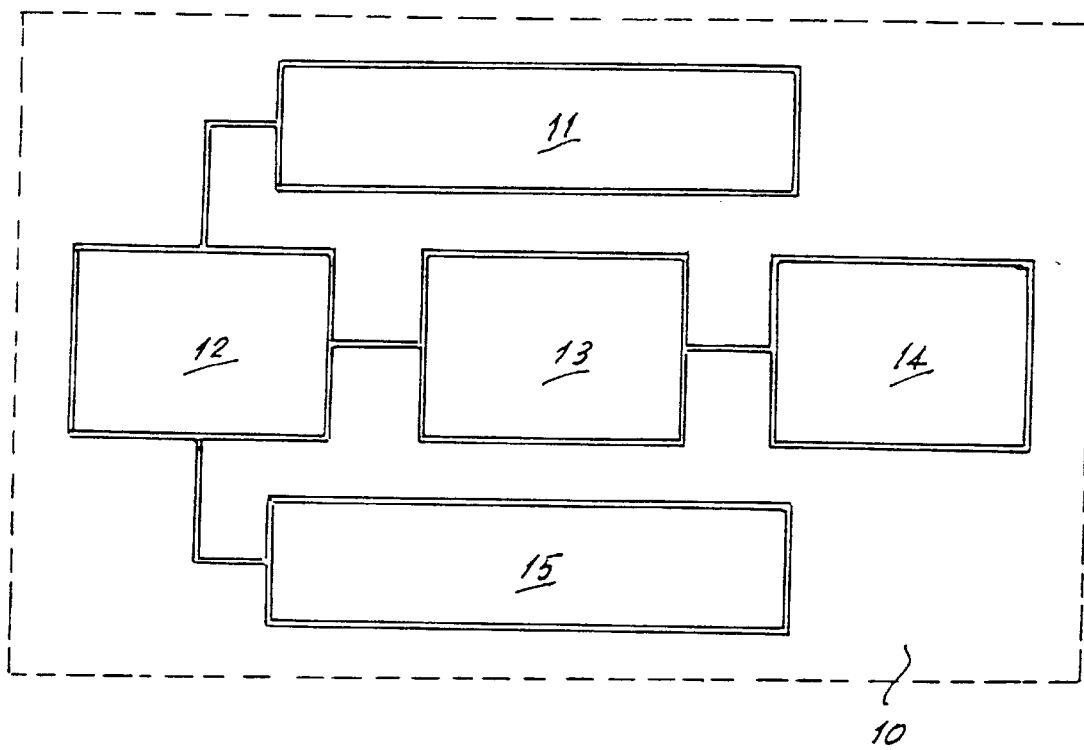
FIG. 1 shows a block diagram with the main elements of the equipment (10).

According to one of the preferred embodiments to be seen in the block diagram of FIG. 1, reference numeral (11) shows a display for the operating parameters for the equipment. The equipment is connected to a control system (12) for a power source (13) and for the multiple ultrasonic waves transducers (14). Both the introduction of data and the control system are governed by a keyboard (15).

The control system (12) uses a microprocessor which carries out all of the monitoring and control tasks of the system. The entry of parameters and data is to be carried out by means of the keyboard (15) and the monitoring is carried out on a viewer (11) usually to be constituted by a liquid crystal display. The multiple ultrasonic waves transducer (14) is directly applied to the area of the body to be treated, being connected to a power source (13) regulatable by the control system (12).

Figure 2:
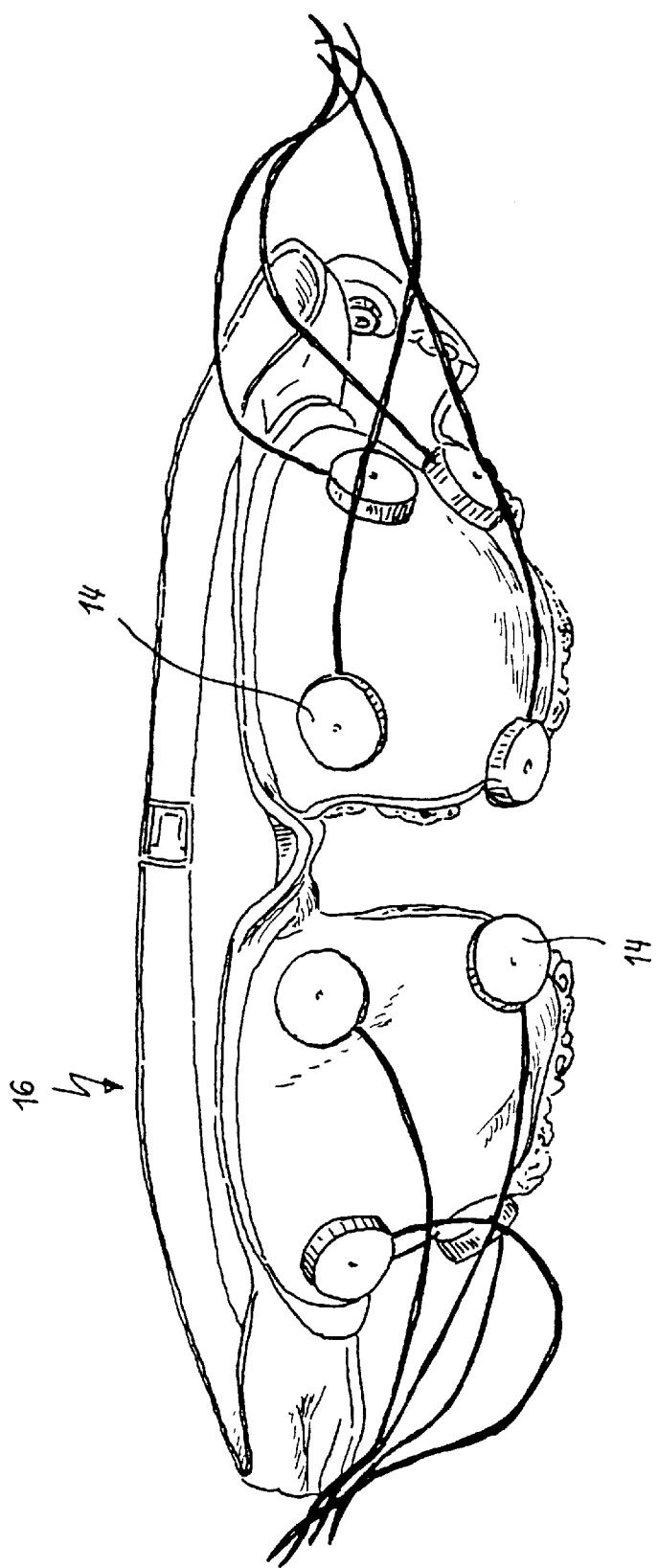
FIG. 2 shows a perspective view of the attachment means for the transducers (14).

The transducers (14) as shown in FIG. 2 are to be located by means of the harness (16) permitting its application on the breasts of the patient. The embodiment shown in FIG. 2 is only one of the possible embodiments of the invention although it is not unique, as the treatment may be optionally carried out on:
Both breasts at a time.
On the right breast.
On the left breast.

Also depending on the type of implant, the transducers (14) will be located on the upper region or on the lower region of the holding means to permit the treatment of the implants in subglandular or in retropectoral situation.

The transmission of energy to the transducers (14) may be optionally carried out as follows:
With the same power input for all of the transducers.
With the same power input for the transducers corresponding to one of the sides (right or left breast).
With different power for each of the sides.
With different power for the transducers located in the upper region in relation to those located in the lower region.

The process for the application of the equipment taking into account the type of the implant and the degree of contracture according to the Baker scale will comprise at least the following steps:
Selection of one of the two working modalities, i.e., continuous or pulsating modes.
Selection of the power supply to transducers (14).
Distribution of power to the transducers (14).
Selection of the working frequency.

The duration and the frequency of the application of the ultrasonic waves will depend on the degree of contracture and in all cases they will be related to the tests which have been described in this specification and to the values expressed in the tables contained in the same.

Although the invention has been sufficiently described according to the above specification and the attached drawings it will be understood that it may possibly be submitted to any modifications necessary without altering the scope of the present invention which will be summarised in the following claims.

We claim:
1. Equipment for the treatment of capsular contractures in a mammal breast implant comprising a support adapted to position supported transducers adjacent to a site of said breast implant, a plurality of transducers which emit ultrasonic wave energy adjustable within a power range of 1 to 15 watts and supported by said support, a power source connected to said transducers, a control adapted to a regulate the power transmitted from the power source to each transducer and a display communicating with the control adapted to display parameters associated with the power source and transducers.

2. Equipment according to claim 1, further having a switch adapted to provide power to the transmitters in a continuous or pulsating mode according to the switch configuration.

3. Equipment according to claim 2, in which the control comprises a microprocessor and a keyboard for the introduction of parameters and data and in which the display is a liquid crystal display.

4. Equipment according to claim 3, in which the working frequency is between 0.5 and 7 MHz.

5. A method for the treatment of capsular contractures in a mammal breast implant which comprises applying ultrasonic energy with a power in the range of 1–15 watts to at least one site external of the mammal body and adjacent to the breast implant.

6. The process of claim 5, in which the application of the ultrasonic energy is continuous.

7. The process of claim 5, in which the application of the ultrasonic energy is discontinuous.

8. The process of claim 5, in which the ultrasonic energy is generated by a plurality of transducers each of which is independently controllable.

9. The process of claim 8, in which the power supplied to at least two transducers is the same.

10. The process according to claim 8, in which the power supplied to at least two transducers is different.

11. The process of claim 8, in which each transducer is connected through a control system to a power source and parameters associated with at least one of the power source and a transducer is displayed in viewable form.

12. The process of claim 8, in which the working frequency of the transducers is between 0.5 and 7 MHz.

* * * * *